US00PP10308P

United States Patent [19]

Wolters et al.

[11] Patent Number: Plant 10,308

[45] Date of Patent: Mar. 31, 1998

[54] ROSEMARY PLANT NAMED 'SILVER SPIRES'

[76] Inventors: Christine P. Wolters; Christian H. Wolters, both of Mayfields, Whitmoor Lane, Sutton Green, Guildford, Surry GU4 7QB, England

[21] Appl. No.: 674,716

[22] Filed: Jul. 2, 1996

[30] Foreign Application Priority Data

Oct. 19, 1995 [GB] United Kingdom ..... 23/175

[51] Int. Cl.[6] ..... A01H 5/00

[52] U.S. Cl. ..... Plt./54.1

[58] Field of Search ..... Plt./54.1

[56] References Cited

U.S. PATENT DOCUMENTS

P.P. 9,124 5/1995 Johnson ..... Plt./54.1

OTHER PUBLICATIONS

*Rosmarinus officinalis* 'Silver Spires', *The Garden*, Journal of the Royal Horticultural Society, vol. 121, Part 8, Aug. 1996, p. 503.

GTITM UPOV-ROM citation for 'Silver Spires' GB PBR02300140, Oct. 1, 1994.

*Primary Examiner*—James R. Feyrer

*Assistant Examiner*—Kent L. Bell

*Attorney, Agent, or Firm*—Burns, Doane, Swecker & Mathis, L.L.P.

[57] ABSTRACT

A new and distinct variety of Rosemary, *Rosmarinus officinalis*, was discovered while growing in a planting area located at Guildford, Surrey, England containing plants of the same species. The origin at the new plant otherwise is unknown. The new variety exhibits distinctive decorative lance-shaped bicolored leaves of pale green and white. Good winter hardiness and resistance to diseases have been observed to date. The new variety propagates well from cuttings and is particularly well suited for serving ornamental as well as culinary uses.

7 Drawing Sheets

SUMMARY OF THE INVENTION

The present invention relates to a new and distinct variety of Rosemary, *Rosmarinus officinalis*, that has been named 'Silver Spires'.

The new variety of the present invention was discovered and selected during 1986 or 1987 from among Rosemary plants of the same species growing outdoors in the ground at our nursery located at Guildford, Surrey, England. The distinctive nature of the new plant is of unknown causation. We were attracted to the new variety primarily becuase of the distinctive appearance of its foliage that differed from that of all other Rosemary plants of which we are aware. Had we not discovered and preserved this new plant it would have been lost to mankind.

It was found that the new variety of *Rosmarinus officinalis:*

(a) exhibits a generally upright growth habit,
(b) forms distinctive narrow lance-shaped bicolored foliage that is pale green and white in coloration,
(c) exhibits good winter hardiness,
(d) exhibits good disease resistance, and
(e) is well suited for culinary as well as decorative uses.

The bicolored foliage is particularly noteworthy and can be used to distinguish the new variety from all previously known varieties. For instance, the pale green/white foliage of the new variety can be readily distinguished from the green/yellow foliage of the previously known 'Aureus' variety (non-patented in the United States). Such distinctive foliage coloration of the new variety is exhibited by plants of all ages.

The new variety of the present invention offers those interested in growing Rosemary plants an opportunity to display a decorative ornamental plant while still forming foliage having customary culinary end uses. The plant can be grown singly, in a mass planting, or as a hedge. Typical Rosemary growing conditions generally can be utilized. Commonly, no special growing conditions are required; however, the plant thrives and does best when growing in well-drained soil under a sunny exposure.

Specimens of the plant when grown in the open field at Guildford, Surrey, England for in excess of five years have well withstood with customary winter conditions of the area with no visible damage. Also, the new variety is believed to well tolerate higher summer temperatures than customarily experienced during the summer months in South East, England.

No disease or pest problems have been observed to date.

Asexual propagation of the new variety has been successfully carried out for a number of years at Guildford, Surrey, England. Rooted cuttings have repeatedly demonstrated that the characteristics of the new variety as discussed herein are firmly fixed and are retained through successive generations of asexual propagation.

BRIEF DESCRIPTION OF THE PHOTOGRAPHS

The accompanying photographs show as nearly true as it is reasonably possible to make the same in color illustrations of this character, typical specimens of the new variety. The plants depicted were reproduced by cuttings and were grown in pots at Guildford, Surrey, England.

Figure 1:
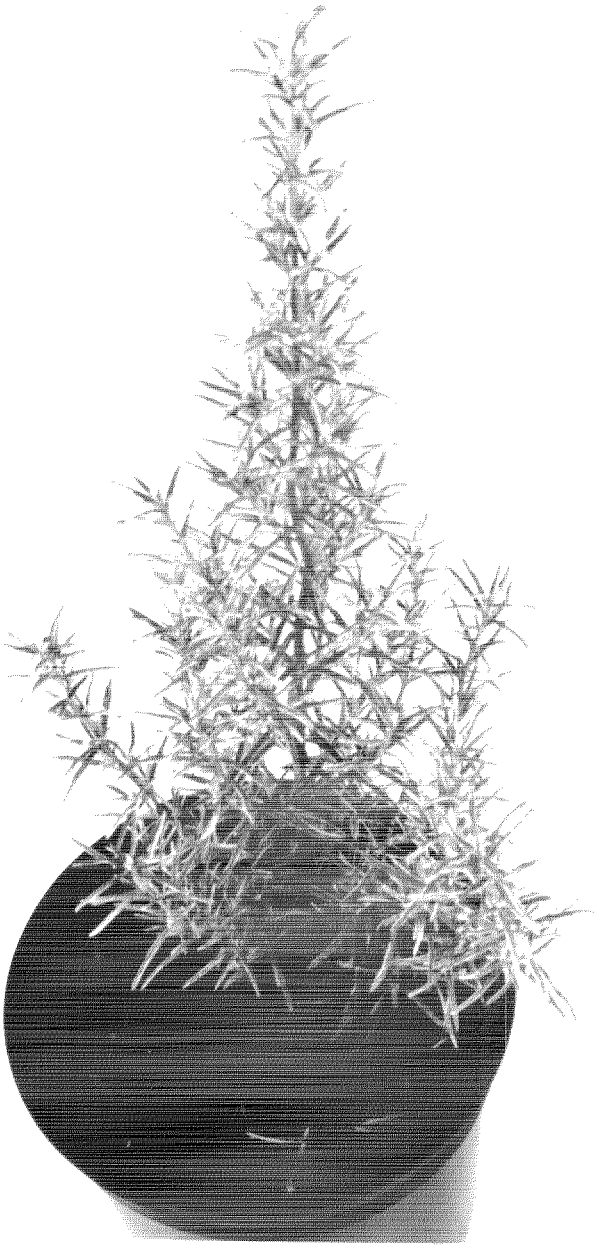
FIG. 1 illustrates the generally upright growth habit of a typical young plant of the new variety. The distinctive bicolored pale green and white foliage is visible.
Figure 2:
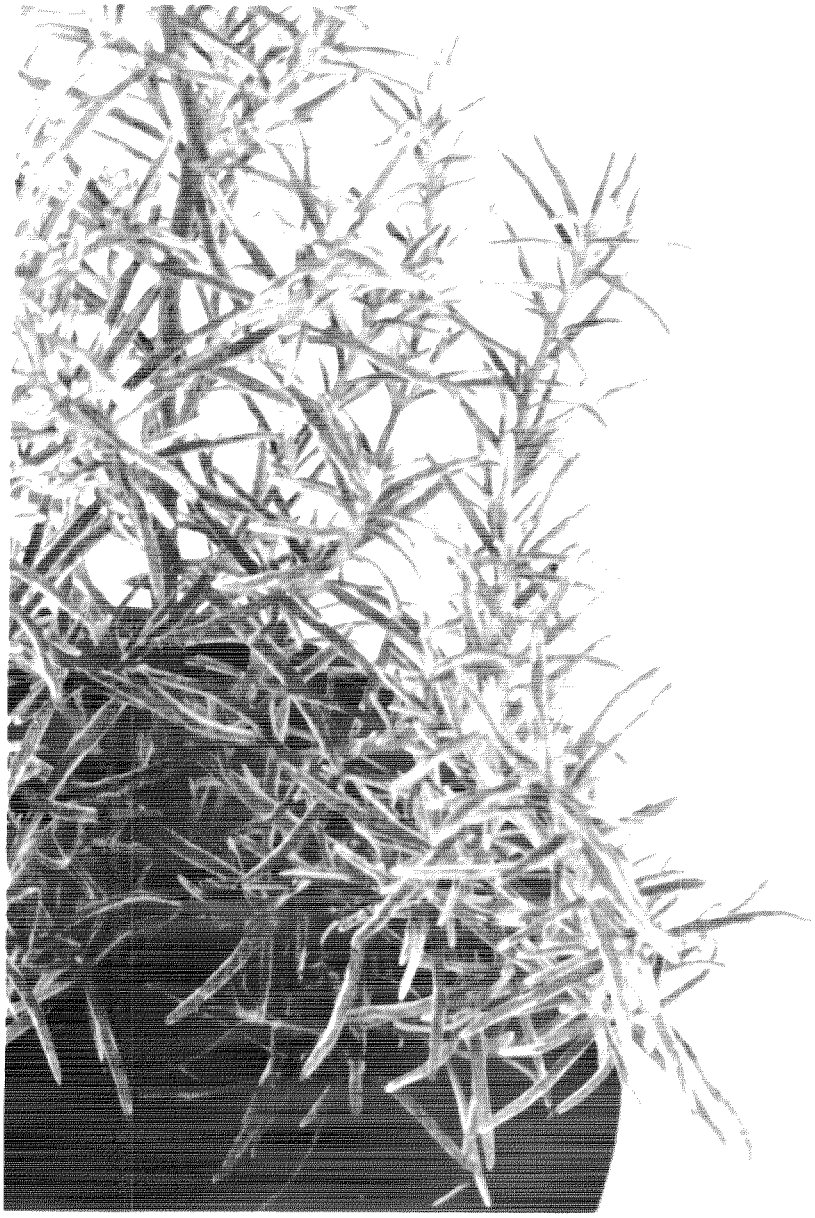
FIG. 2 illustrates a closer view of the narrow bicolored lance-shaped leaves of the new variety while generally viewing downwardly towards a portion of a young plant.
Figure 3:
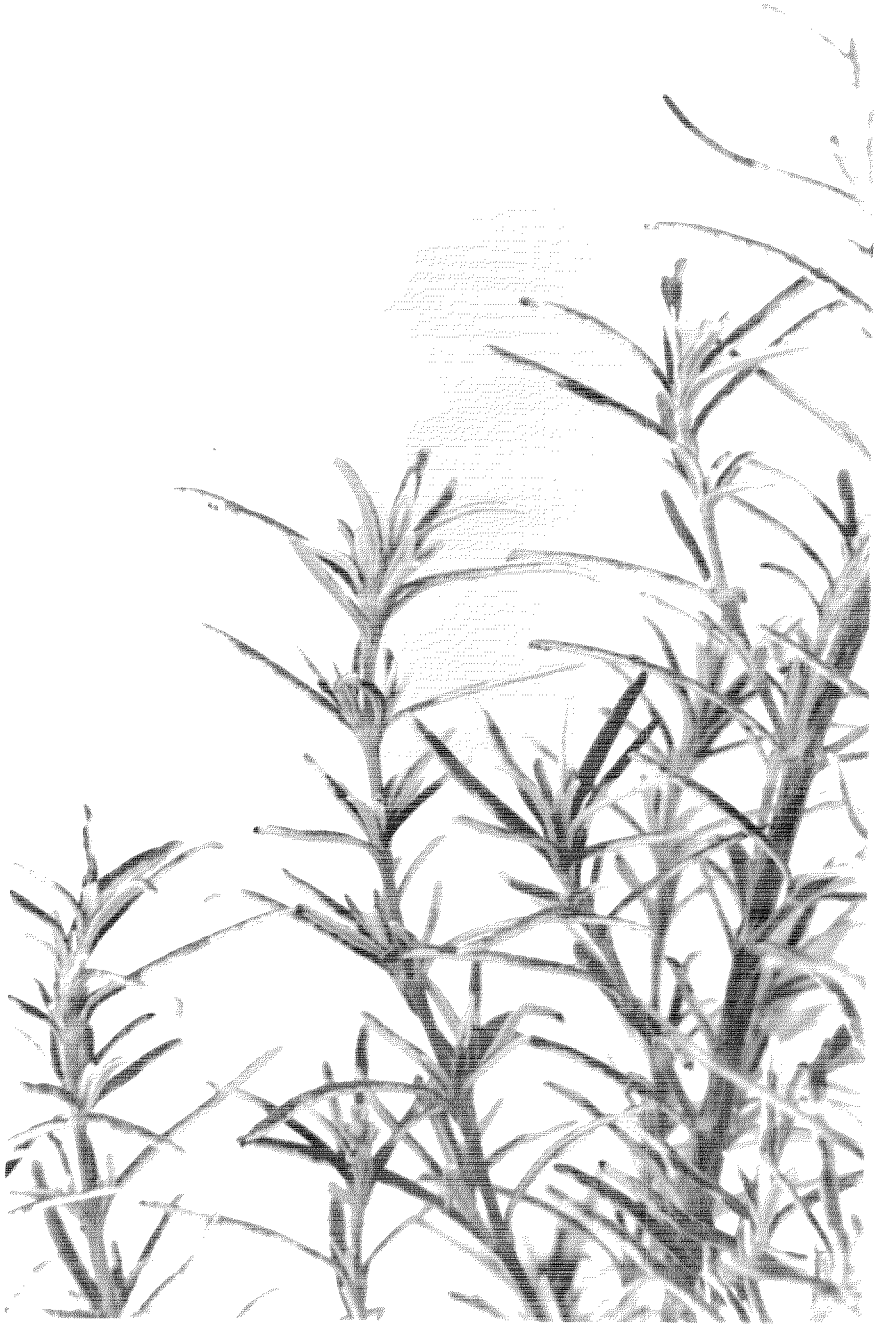
FIG. 3 illustrates a further view of the foliage of the new variety as seen generally from the side. The under surfaces of typical leaves of a young plant of the new variety are visible.
Figure 4:
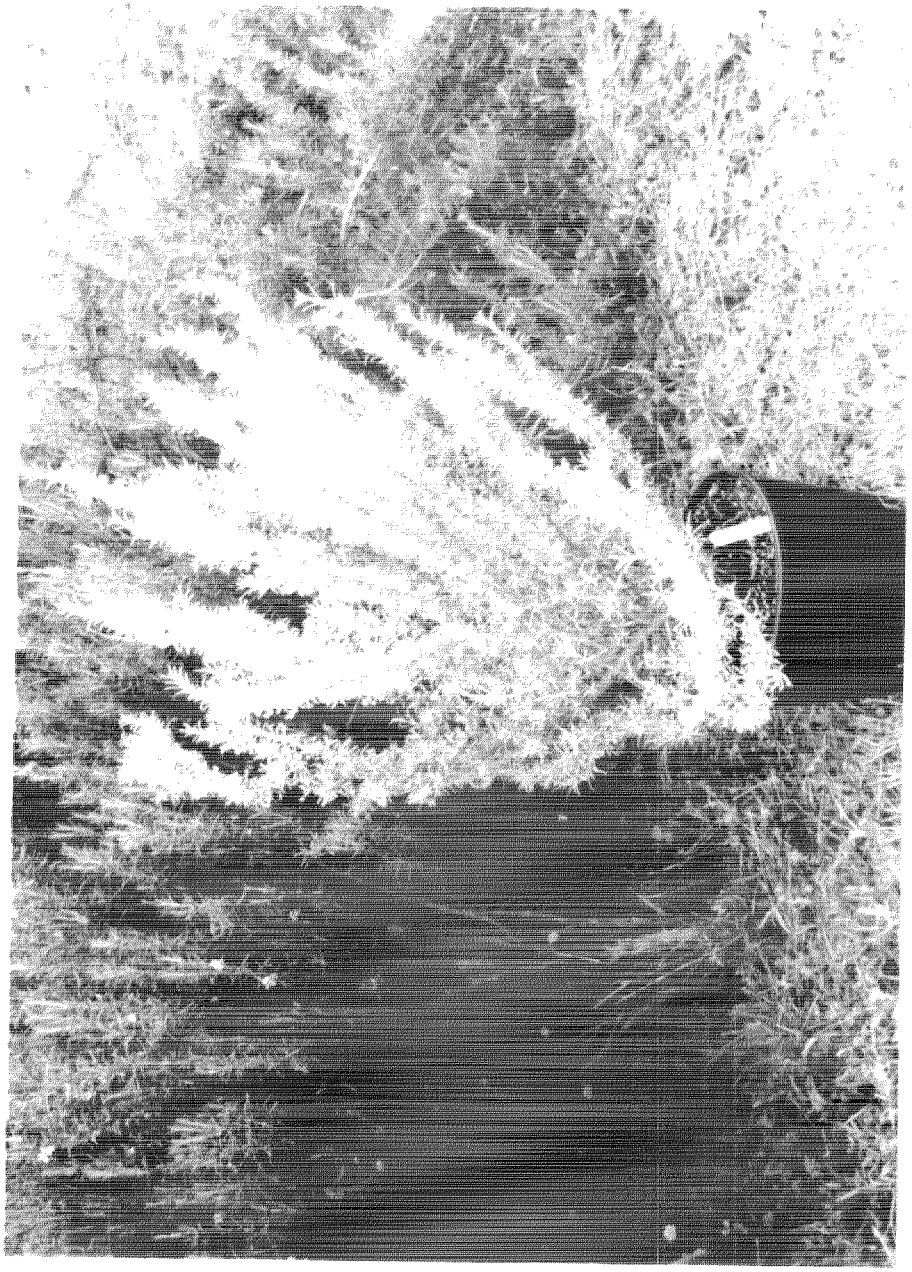

FIG. 4 illustrates at the center while growing in a pot during the springtime a four-year old plant of the new variety. The bright sunlight causes the foliage and particularly the newer shoots to appear almost white when viewed from a distance. Typical mature *Rosmarinus officinalis* plants are shown in the background wherein the customary Rosemary foliage coloration is visible.

Figure 5:
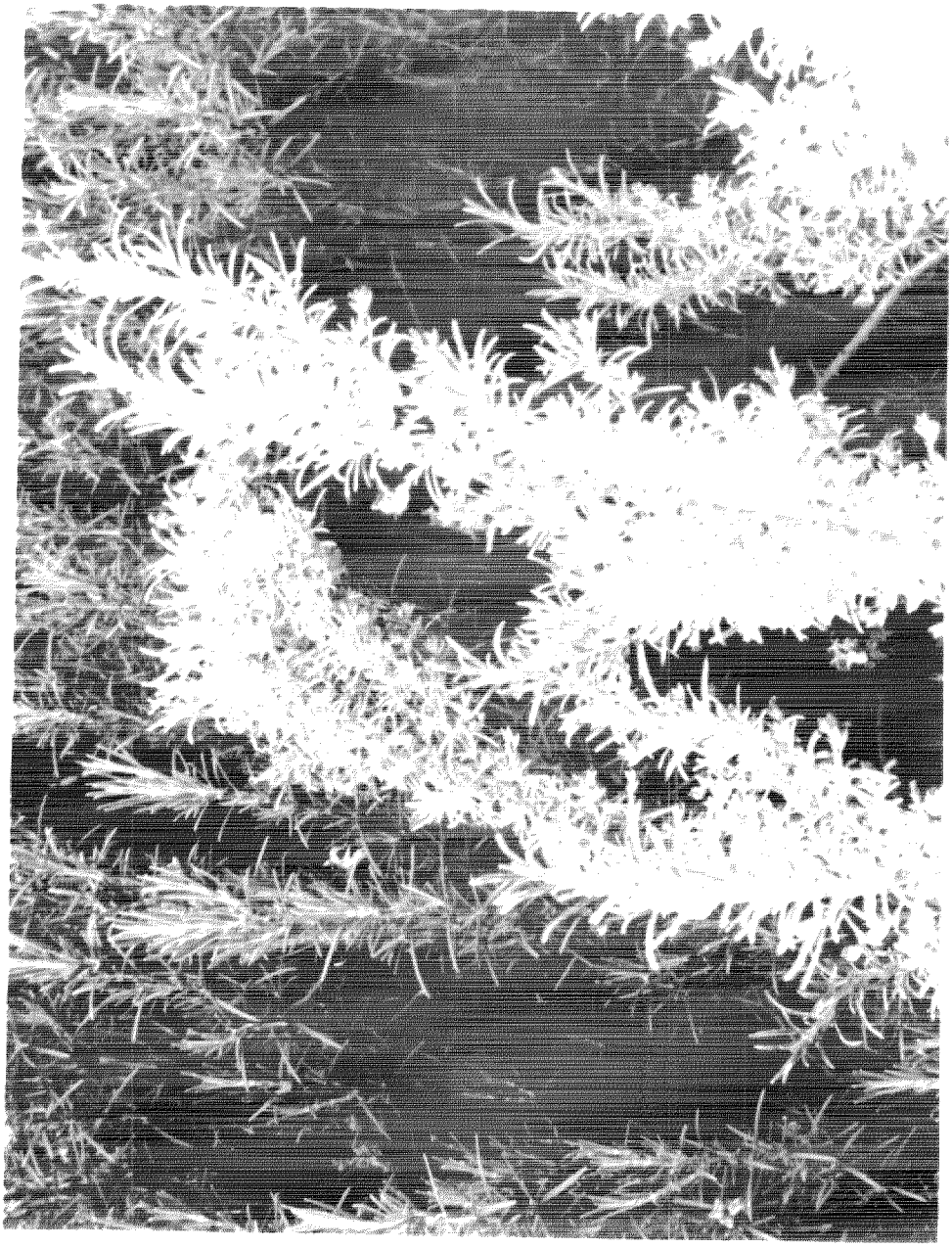

FIG. 5 illustrates a closer view of the foliage present on a portion of the same plant illustrated in FIG. 4. A few remaining flowers are visible. The foliage of the typical *Rosmarinus officinalis* plants continues to be visible in the background.

Figure 6:
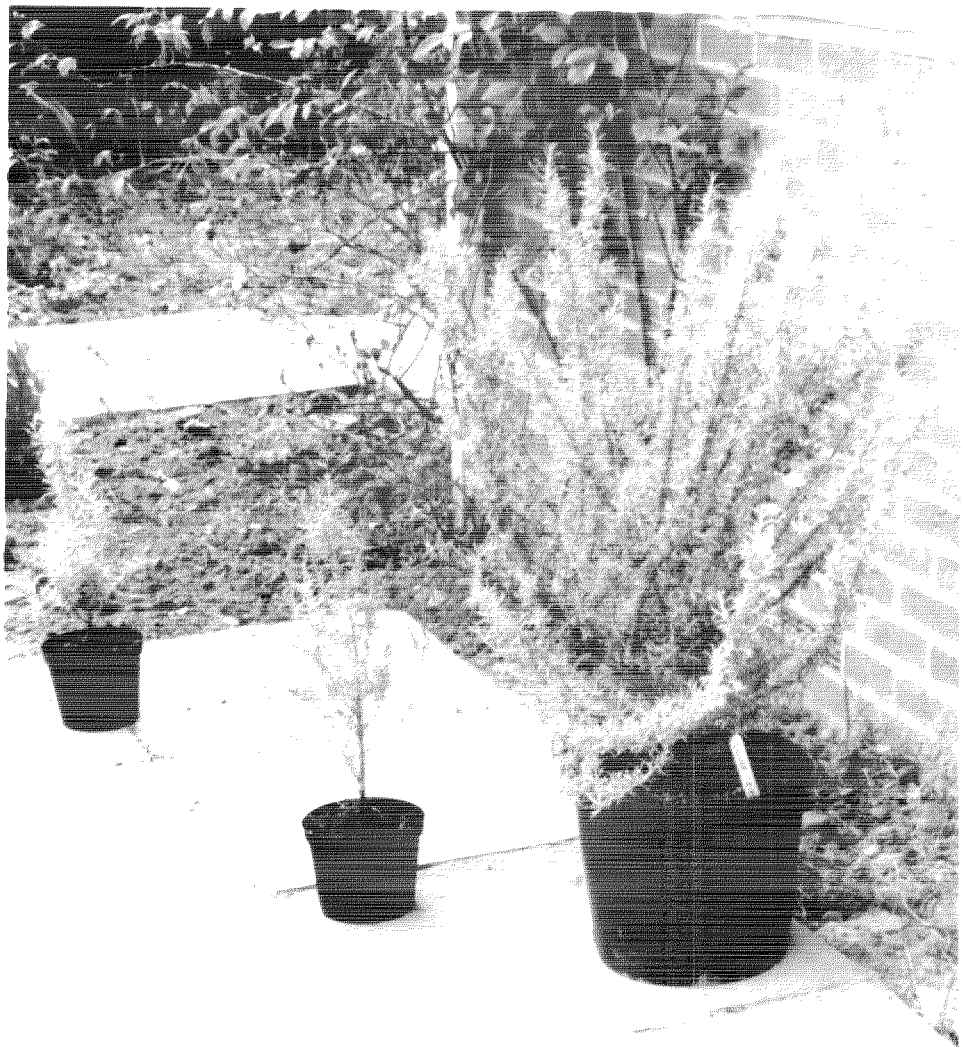

FIG. 6 illustrates at the left while growing in pots two young 18-inch plants of the new variety and at the right the same four-year old plant of the new variety that is illustrated in FIGS. 4 and 5. The longest stem of the four-year old plant measures approximately 33 inches.

Figure 7:
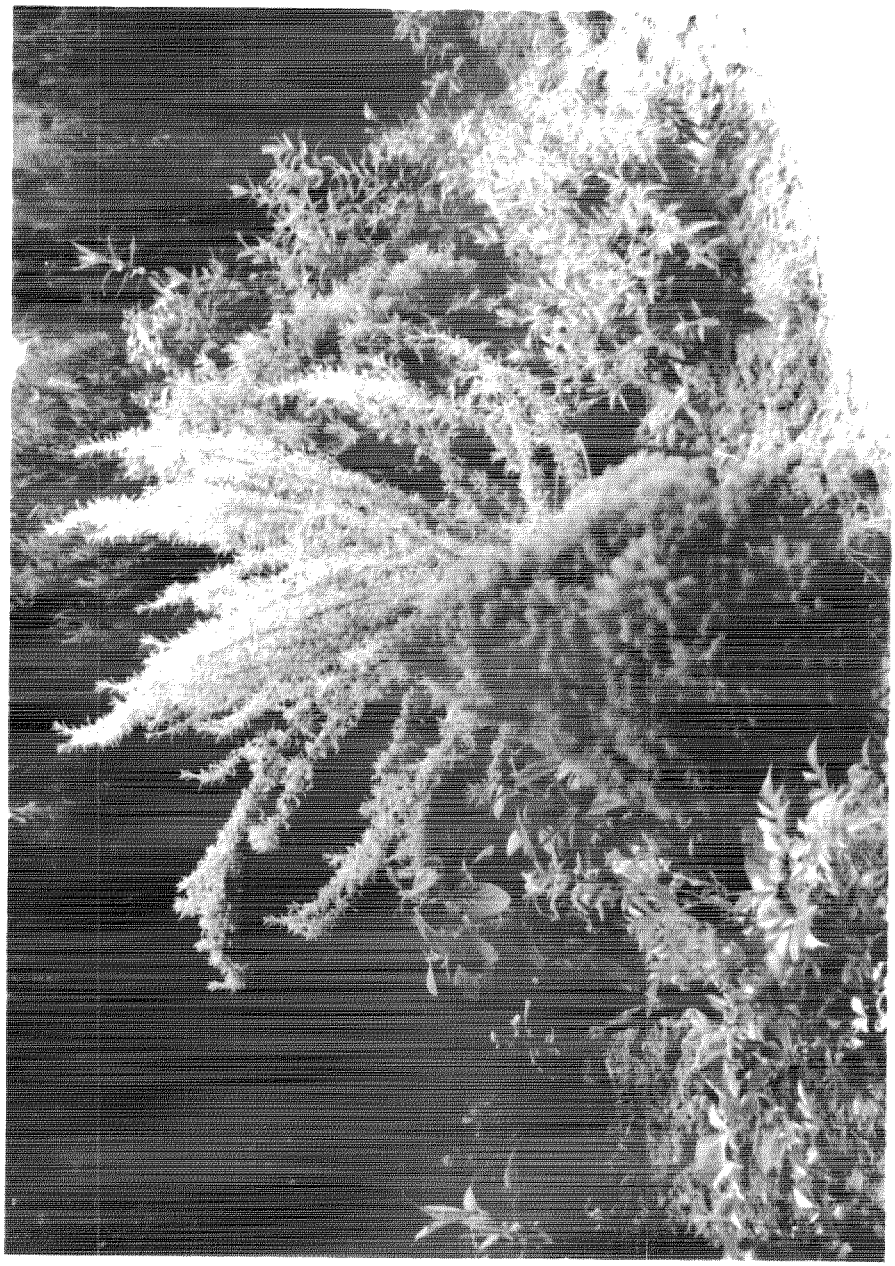

FIG. 7 illustrates at the center a plant of the new variety while growing in a pot and positioned among other well-known shrubs. Significant differences in foliage coloration and texture are visible.

DETAILED DESCRIPTION

The chart used in the identification of color is the *R.H.S. Colour Chart* of The Royal Horticultural Society, London, England. The following observations were prepared from the study of plants reproduced from cuttings and growing in pots at Guildford, Surrey, England.

Classification: *Rosmarinus officinalis*, 'Silver Spires' variety.

Foliage:

*Type.*—Evergreen.

*Stems.*—Pale green, Green-White Group 157A, on young shoots, turning to brown, Greyed-Orange Group 165B.

*Leaf configuration.*—Simple, linear, lance-shaped.

*Leaf size.*—Approximately 20 to 30 mm. in length, and approximately 1.5 to 2.5 mm. in width.

*Leaf color young leaves.*—When expanding green, Green Group 137A to 137B, and somewhat irregularly overlaid and margined with white, White Group 155A.

*Leaf color mature leaves.*—On the upper surface green, Green Group 137A to 137B, and somewhat irregularly overlaid and margined with White, White Group 155A. On the under surface pale green, Green-White Group 157A and somewhat irregularly overlaid and margined with White, White Group 155A.

Flowers:

*Time.*—Once during Springtime.

*Type.*—Single, and substantially the same in size and coloration as those of typical *Rosmarinus officinalis* plants.

*Arrangement.*—Clustered, axilliary corymbs.

Plant:

*Type.*—Shrub.

*Growth habit.*—Upright.

*Growth.*—Medium.

*Disease resistance.*—Good.

*Winter hardiness.*—Good.

We claim:

1. A new and distinct variety of *Rosmarinus officinalis* plant which:

(a) exhibits a generally upright growth habit,
(b) forms distinctive narrow lance-shaped bicolored foliage that is pale green and white and in coloration,
(c) exhibits good winter hardiness,
(d) exhibits good disease resistance, and
(e) is well suited for culinary as well as decorative uses;

substantially as herein shown and described.

* * * * *